United States Patent [19]

Watts, Jr. et al.

[11] 4,148,819
[45] Apr. 10, 1979

[54] ALIPHATIC DIISOCYANATES

[75] Inventors: Lewis W. Watts, Jr., Austin; Clifford L. Lambert, Jr., Georgetown; Edward T. Marquis, Austin, all of Tex.

[73] Assignee: Texaco Development Corp., New York, N.Y.

[21] Appl. No.: 892,523

[22] Filed: Apr. 3, 1978

[51] Int. Cl.$^2$ .......................................... C07C 119/042
[52] U.S. Cl. ...................... 260/453 AL; 260/153 PH; 260/584 B; 568/617; 521/162
[58] Field of Search ...................... 260/453 AL, 584 B

[56] References Cited

U.S. PATENT DOCUMENTS

| | | | |
|---|---|---|---|
| 3,370,077 | 2/1968 | Hartzell | 260/453 AL |
| 3,631,199 | 12/1971 | Smith et al. | 260/453 AL |

*Primary Examiner*—Dolph H. Torrence

*Attorney, Agent, or Firm*—Carl G. Ries; Thomas H. Whaley; James L. Bailey

[57] ABSTRACT

Covers a diisocyanate having the following structural formula:

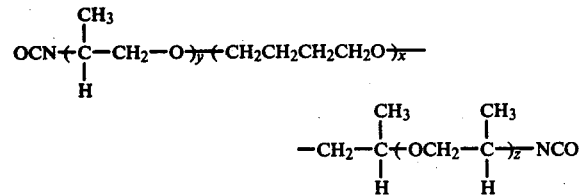

where x is an average number ranging from about 6 to 50, and y and z are average numbers ranging from about 1 to about 20, with the sum of y and z being from about 6 to about 40. Also covers a method of preparing said diisocyanate.

9 Claims, No Drawings

ALIPHATIC DIISOCYANATES

BACKGROUND OF THE INVENTION

1. Field of the Invention

This invention is concerned with aliphatic diisocyanates useful as polyurethanes. The present invention is also concerned with the process for preparing said diisocyanates.

2. Description of the Prior Art

A wide variety of both aliphatic and aromatic di- and higher polyisocyanates have been disclosed, as well as diverse methods of their preparation. In many instances such isocyanates are difficult and/or uneconomical to prepare. In yet other cases the amine precursors to the isocyanates have to be prepared in steps involving acid neutralization and removal of subsequent salt formation. For example, polymeric polyisocyanates are prepared by first preparing the polyamines via a reaction involving neutralization with base followed by salt removal. More specifically, aniline is reacted with formaldehyde in the presence of a strong mineral acid such as hydrochloric acid to provide a reaction mixture which upon neutralization with a base may be treated to recover polyphenylamines. It is necessary to utilize large quantities of both a mineral acid and base which adversely affect the economics of the process and also the ease in conducting the reaction. In addition, use of large quantities of mineral acids and bases presents a severe corrosion problem.

It therefore would be an advance in the art to provide a new class of diisocyanates prepared directly from a diamine whose preparation does not involve the just-mentioned drawbacks.

SUMMARY OF THE INVENTION

In its broadest aspects the present invention provides a novel class of diisocyanates having the following structural formula:

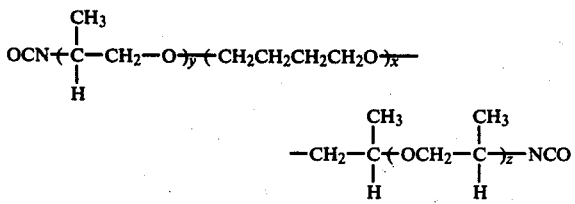

where x is an average number ranging from about 6 to 50, and y and z are average numbers ranging from about 1 to about 20, with the sum of y and z being from about 6 to about 40.

DETAILED DESCRIPTION OF THE INVENTION

The above diisocyanates may be prepared by any number of methods. One simple, yet unique way of achieving the above diisocyanates is to first prepare the precursor amine and, then directly phosgenate said amines. These amines are prepared as follows.

The first step in the invention involves providing as a starting reactant a polybutanediol having the following structural formula:

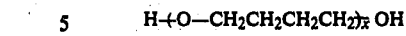

where x is an average number ranging from about 6 to about 50, and propoxylating said polybutanediol with sufficient propylene oxide to provide an adduct having the structure:

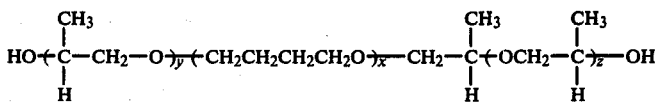

where y and z are average numbers ranging from about 1 to about 20 with the sum of y and z being from about 6 to about 40. More often the sum of y and z is 6–20 and most preferably is 6–10. X is an average number ranging from about 6 to about 50 and more often ranges from about 8 to about 40.

Starting diols of the above type which can be propoxylated are commercially available, and need little elaboration. For example, a typical useful starting material of this class is a polyoxybutylene diol sold under the trademark POLYMEG® 100 by Quaker Oats Co. This particular material has an average molecular weight of approximately 1000.

The propoxylation reaction can be conducted using conventional methods and conditions such as temperatures in the range of about 40° to about 200° C. and pressures ranging from about 0 to about 100 psig. Usually the reaction occurs under basic conditions established through the use of alkali metals, their hydroxides, oxides and hydrides and in some cases basic amines. Representative alkoxylation procedures which may be followed here are described in the following reference. Martin J. Schick, Ed. "Nonionic Surfactants," Marcel Dekker Inc., New York, N.Y. 1967, pp. 187–204. It is necessary of course, that sufficient propylene oxide be added to the polybutanediol to provide a propoxylated product wherein y+z is at least six.

It is interesting to note that one cannot directly aminate the polybutanediol by means of conventional reductive amination catalysts such as a nickel-based catalyst. It was discovered here that when such direct reductive amination is carried out hydrogenolysis occurred. Thus, in order to avoid such hydrogenolysis it was found that the primary alcohol must be transformed into a secondary alcohol by means of the propylene oxide reaction to make the resultant diol amenable to reductive amination.

The propylene oxide adduct is then reacted with ammonia or ammonia hydroxide in presence of a suitable reductive amination catalyst to produce the desired polymeric amine. A wide number of known catalysts of this type are useful here. Preferred are nickel and cobalt-based catalysts, with the most preferred being a nickel-based catalyst, including Raney nickel and nickel in combination with other metals or oxides of metals.

The above-described propylene oxide adducts are reacted with ammonia or ammonium hydroxide (preferably ammonia) in the presence of said hydrogenation-dehydrogenation catalyst at elevated temperatures in the presence of hydrogen to form the amines. Suitable reactors include either a closed autoclave resulting in a batch process or a tubular reactor which can be operated in a continuous manner. Either is suitable for the practice of this invention.

As just noted the class of useful catalysts here is well known and may include one or more of the metals including copper, nickel, cobalt, chromium, aluminum, maganese, platinum, palladium and rhodium and the oxides of these metals. The metals or their oxides may be employed in combination with normally nonreducible metal oxides such as chromium oxide, molybdenum oxide and manganese oxide. The amount of the nonreducible oxide employed may be varied considerably and some catalysts, notably those based upon cobalt require the presence of no nonreducible metal oxides.

One preferred catalyst that is very effective for the amination reaction, includes the metals or oxides of nickel, cobalt and chromium. A particularly satisfactory catalyst is one in which the active ingredients consist essentially, in mole percentages on an oxide-free basis of 60–85 percent nickel, 14–37 percent copper and 1–5 percent chromium as produced in accordance with procedures described in U.S. Pat. No. 3,152,998. As used herein this catalyst will be referred to as a nickel-copper-chromium catalyst.

The reductive amination reaction is carried out from 160° to 250° C. The reaction pressures are from 750 to about 4000 psig with a hydrogen partial pressure of at least 200 psig. The preferred pressure range is from about 1000 to about 2500 psig and a hydrogen partial pressure from about 200 to about 2000 psig.

The residence time in the reactor to be used to produce the amine polymers are those which would occur at space velocities of about 0.2 to about 3.0 volume of reactants per volume of catalyst per hour, with the preferred space velocity being from about 1.0 to about 2.0. The space velocity herein described is in cm$^3$/volume of catalyst/hour, but rates in equivalent units are equally applicable.

The ratio of reactants, i.e., propylene oxide adducts and the ammonia can vary over a wide range to produce the amines. The feed rate of the adduct expressed here in terms of lbs. per hour, can vary from about one times the ammonia feed rate to from about 0.2 times the ammonia feed rate.

By following the above-discussed techniques of the invention substantially all of the hydroxyl groups of the propylene oxide adduct are transformed into primary amine groups.

The above polymeric diamine may then be phosgenated via any number of known techniques. In a preferred procedure the amine is dissolved in a chlorinated aromatic hydrocarbon and this solution is added at a temperature within the range from about 25° to about 50° C. to a chlorinated aromatic hydrocarbon solution of phosgene containing from about 4 to 5 mole equivalents of phosgene per mole equivalent of amine group in the amine feedstock. After the addition is complete the resultant slurry is heated, which heat reaction step may be conducted at atmospheric or super-atmospheric pressure sufficient to maintain the solvent in liquid phase at the reaction temperature employed. The temperature is suitably within the range of from about 75° to 150° C. depending upon the pressure point of the solvent and is more preferably conducted at atmospheric pressure at about 100° C. to about 140° C. An additional mole or two of phosgene is added during the heat-up and hot reaction steps. When a clear solvent solution of the polyisocyanate reaction product is obtained (indicating decomposition of intermediate carbamoyl chlorides), the reaction is terminated and the chlorinated aromatic hydrocarbon removed in any suitable manner such as by flash distillation or vacuum distillation.

The resultant diisocyanate is extremely useful as a component useful in forming polyurethanes such as polyurethane foams, castings, prepolymers, etc.

The above described invention is more particularly set forth in the following Examples which are to be construed for purposes of illustration only and not for limitation of the invention. Obvious modifications of the following Examples can be made.

EXAMPLE I

A polyoxybutylene diol (POLYMEG ® 1000, available from Quaker Oats Co.) of a molecular weight of approximately 1000 was provided in an amount of 500 grams (0.49 mole). To this was added 10.0 grams potassium hydroxide, and the mixture placed in a 1-liter autoclave. Propylene oxide in an amount of 60.0 grams, 1.03 moles, was slowly added to the hot (120° C.) mixture of basic diol. After digesting the resultant reaction mixture at 120° C. for ½ hour the product was allowed to cool. The product was then treated with oxalic acid (11 grams of the dihydrate salt), filtered and stripped to 100° C. at 0.2 mm Hg. Nmr data confirmed that the isolated material was the desired propylene oxide adduct.

EXAMPLE II

To a 10 gal. stirred reactor was charged 30.0 lbs. of a polybutanediol (POLYMEG ®, available from Quaker Oats Co. of approximately 1000 molecular weight) and 50.0 grams of potassium hydroxide. Upon heating to 130° C. there was added 22.0 lbs. of propylene oxide over a period of 3 hours. After digesting for 2 hours at 130° C., followed by cooling, neutralizing with citric acid (120 grams), stripping under reduced pressure, and filtering, there was isolated an essentially colorless mobile liquid having a hydroxyl number of 108 mg KOH/g sample. The product was a 6.7 mole propylene oxide adduct.

EXAMPLE III

To a 500 ml high pressure reactor system there was charged 500 grams of a prereduced, pelleted nickel-copper-chromium catalyst containing 75 mole percent nickel, 23 percent copper and 2 mole percent chromium. The propylene oxide adduct of Example II was introduced at the rate of 0.393 lbs./hr. along with anhydrous ammonia at 0.81 lbs./hr., and hydrogen at 76 lbs./hr. The reaction temperature was 206°–214° C., the reaction pressure was 2550 psig, and the liquid hourly space velocity was 1.09.

After stripping the resulting crude product at 100° C. and 0.2 mm Hg. there was isolated an essentially colorless liquid. The total acetylatables of this liquid was 1.95 meq/gm (theory, 1.98). The total amines was 1.72 meq/gm (theory, 1.98), and the primary amines was 1.69 meq/gm (theory, 1.98). The percent of primary amines was 98.3%, demonstrating the unexpected substantially complete conversion of the terminal hydroxyl groups to primary amine terminal groups.

EXAMPLE IV

Phosgenation of the polymeric amine of Example III was carried out as follows. To a 5 liter, round bottom flask was added 1500 ml. chlorobenzene. The flask was cooled to 0°–15° C. with nitrogen sweeping to keep out moisture. To the cold chlorobenzene was added 400 g. phosgene, followed by the dropwise addition of an amine solution comprising 105.0 g of the polymeric amine of Example III diluted with 1000 ml. chlorobenzene. The amine addition required 12 minutes and the temperature of the reaction period during this addition rose from 7° C. to 17° C. The reaction mixture was slowly heated to 120° C. over a 1 hour and 33 minute period. During heat-up, phosgenation of the amine was aided by the continued addition of phosgene below the liquid surface of the reaction mixture. Thus, approximately 200 g. of additional phosgene was added during the heat-up. The reaction mixture was held at 120° C. for approximately 1 hour during which time 20 g. of additional phosgene was added. Thereafter, a clear, water-white reaction mixture was obtained.

The crude, dilute reaction mixture was stripped of phosgene and chlorobenzene first at aspirator vacuum. The aspirator vacuum was used up to a 105° C. pot temperature. At this 105° C. temperature the stripping was switched to a high vacuum condition. The pot temperature was allowed to reach 148°–168° C. and held there for 21 minutes at 1.2–1.3 mm Hg vacuum. The weight of the stripped product was 109.6 g.

The product isocyanate analyzed as follows: Acidity (wt. % HCl) — 0.14; hydrolyzable chloride (wt. % Cl) HCl — 0.20; total chloride (wt. % Cl) — 0.65; NCO meq/g — 1.63; Brookfield viscosity, cps at 25° C. —210.

The isocyanate content of 1.63 meq/g closely agreed with the theoretical isocyanate content of 1.65 meq/g.

In a comparative run a product exactly similar to that of Example IV was prepared with the exception that it was derived from a three mole propylene oxide adduct, i.e., y+z is three. This isocyanate was definitely inferior in quality to the 6.7 mole adduct in that acidity and chloride were higher and % NCO based on theory was lower. Specifically the NCO content was 1.83 meq/g, acidity was 0.21 wt. % HCl, hydrolyzable Cl was 0.20 wt. % Cl, total Cl was 1.11 wt. % Cl, and % NCO observed/(theory × 100) was 78.5% versus a 98.8% figure of Example IV.

Thus, it is important that the amount of propylene oxide content be high enough in the products of this invention such that y+z is six or more. Products of surprising quality are thus produced, having special utility as components of polyurethane foams.

We claim:

1. A composition comprising a diisocyanate having the following structural formula:

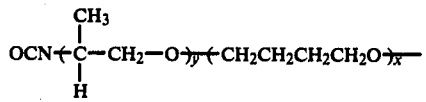

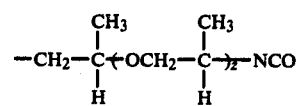

where x is an average number ranging from about 6 to 50, and y and z are average numbers ranging from about 1 to about 20, with the sum of y and z being from about 6 to about 40.

2. The composition of claim 1 where the sum of y and z are 6–20.

3. The composition of claim 2 where the sum of y and z are 6–10.

4. The composition of claim 1 where x equals 8–40.

5. A process of preparing an aliphatic diisocyanate having the following structural formula:

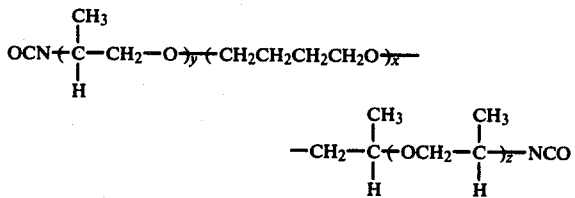

where x is an average number ranging from about 6 to 50, and y and z are average numbers ranging from about 1 to about 20, with the sum of y and z being from about 6 to about 40, which comprises providing a polybutanediol having the structure:

where x is as above and propoxylating said polybutanediol with sufficient propylene oxide to provide an adduct having the structure:

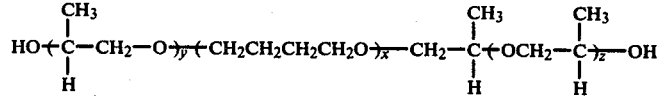

where x, y and z are as above and reductively aminating said adduct with ammonia or ammonium hydroxide in presence of a reducing catalyst to provide a polymeric amine having the structure:

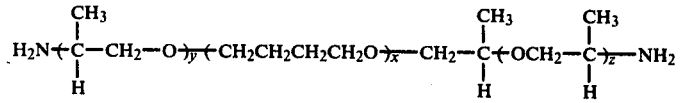

and phosgenating said polymeric amine to provide said diisocyanate.

6. The process of claim 5 wherein said catalyst is a nickel-based catalyst.

7. The process of claim 6 wherein said nickel based catalyst is Raney nickel or nickel-copper-chromium catalyst.

8. The process of claim 5 wherein said propoxylation is carried out to provide an adduct wherein the sum of y and z are 6–20.

9. The process of claim 8 wherein the sum of y and z are 6–10.

* * * * *